(12) United States Patent
McCarthy et al.

(10) Patent No.: US 9,308,102 B2
(45) Date of Patent: Apr. 12, 2016

(54) ACETABULAR CUP POSITIONING DEVICE

(71) Applicant: Howmedica Osteonics Corp., Mahwah, NJ (US)

(72) Inventors: Thomas Francis McCarthy, Neshanic Station, NJ (US); Anthony J. La Rosa, Wharton, NJ (US); Edward J. Laganis, Edgewater, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 417 days.

(21) Appl. No.: 13/783,934

(22) Filed: Mar. 4, 2013

(65) Prior Publication Data

US 2014/0249535 A1    Sep. 4, 2014

(51) Int. Cl.
| | |
|---|---|
| *A61B 17/58* | (2006.01) |
| *A61B 17/60* | (2006.01) |
| *A61F 2/00* | (2006.01) |
| *A61F 2/46* | (2006.01) |
| *A61F 2/34* | (2006.01) |

(52) U.S. Cl.
CPC ............. *A61F 2/4684* (2013.01); *A61F 2/4657* (2013.01); *A61F 2/34* (2013.01); *A61F 2002/4666* (2013.01)

(58) Field of Classification Search
CPC ....... A61F 2/4684; A61F 2/34; A61F 2/4657; A61F 2002/4666
USPC ............ 606/91, 102, 130, 86 R–86 B, 87–89, 606/22.38; 623/22.38; 73/1.77, 488–551; 33/318, 321–323, 365, 366.11–366.14
See application file for complete search history.

(56) References Cited

U.S. PATENT DOCUMENTS

| | | | |
|---|---|---|---|
| 4,305,394 A | 12/1981 | Bertuch, Jr. | |
| 4,475,549 A | 10/1984 | Oh | |
| 4,716,894 A | 1/1988 | Lazzeri et al. | |
| 5,037,424 A | 8/1991 | Aboczsky | |
| 5,061,270 A | 10/1991 | Aboczky | |
| 5,197,488 A | 3/1993 | Kovacevic | |
| 5,417,696 A | 5/1995 | Kashuba et al. | |
| 5,879,401 A | 3/1999 | Besemer et al. | |
| 6,197,032 B1 | 3/2001 | Lawes et al. | |
| 6,245,109 B1 | 6/2001 | Mendes et al. | |

(Continued)

OTHER PUBLICATIONS

US 8,180,424, 05/2012, Selkee (withdrawn)

*Primary Examiner* — Brian Szmal
(74) *Attorney, Agent, or Firm* — Lerner, David, Littenberg, Krumholz & Mentlik, LLP

(57) ABSTRACT

An acetabular trialing system has a trial cup including a body comprising an outer surface, a part-spherical inner surface and a rim extending between the inner and outer surface with a plurality of spaced inwardly resiliently deflectable rim members each connected at a first end to the body outer surface. The part-spherical inner surface has a plurality of spaced resilient deflectable bearing members each forming part of the body part-spherical inner surface. The bearing members have a first end deflectable towards the body outer surface. Upon inward deflection, one of the plurality of deflectable rim members is capable of contacting the first end of a corresponding one of the plurality of deflectable bearing members and moving the bearing member towards the body outer surface and into contact an electrical signaling device mounted on the body intermediate the outer surface thereof and the deflectable bearing member.

24 Claims, 13 Drawing Sheets

(56) References Cited

U.S. PATENT DOCUMENTS

| | | |
|---|---|---|
| 6,395,005 B1 | 5/2002 | Lovell |
| 7,615,055 B2 | 11/2009 | DiSilvestro |
| 7,769,429 B2 | 8/2010 | Hu |
| 7,849,751 B2 | 12/2010 | Clark et al. |
| 8,007,448 B2 | 8/2011 | Moctezuma de La Barrera |
| 8,245,583 B2 | 8/2012 | Stein |
| 8,277,454 B2 | 10/2012 | Neubauer et al. |
| 8,337,426 B2 | 12/2012 | Nycz |
| 2010/0249660 A1 | 9/2010 | Sherman et al. |
| 2010/0249777 A1 | 9/2010 | Sherman et al. |
| 2011/0303424 A1 | 12/2011 | Chang |
| 2012/0283599 A1 | 11/2012 | Borja |

ACETABULAR CUP POSITIONING DEVICE

BACKGROUND OF THE INVENTION

The present invention relates generally to the alignment of an acetabular implant device in connection with the implantation of a prosthetic hip joint in a natural pelvis and pertains, more specifically, to an apparatus and method which utilizes a disposable trial impingement sensor to guide the appropriate alignment of the acetabular device at an implant site in the pelvis.

Many articulating joints of the body, such as the joints of the hips, have anatomical ball and socket connections between bones of the joints providing a wide range of motion. The hip joint, for instance, includes a socket or acetabulum in the pelvis and a femoral head or ball at an upper end of the femur or thigh bone received in the acetabulum. Where natural articulating joints are congenitally defective or become degraded due to disease or injury, prosthetic or artificial ball and socket components are commonly implanted in the body to replace the natural ball and socket structure of the joints. In total joint replacement surgery, prosthetic ball and socket components are both implanted as, for example, in total hip arthroplasty wherein a femoral stem component having a head or ball thereon to replace the natural femoral head is affixed to the femur. A socket or acetabular component having an outer shell member and a bearing insert or liner received in a cavity of the shell is affixed to the acetabulum. The head or ball of the femoral component is rotatably or pivotally received in a socket of the liner to recreate the natural articulation of the hip joint. In subtotal or partial joint replacement surgery, natural bone structure of the joint is left intact to cooperate with an implanted prosthetic component. One example of subtotal joint replacement surgery being a cup arthroplasty wherein a prosthetic acetabular or socket component is implanted in the acetabulum to receive the natural femoral head.

It is extremely important in total or partial joint replacement surgery and, in particular, total and subtotal hip replacement surgery, that the ball and socket components be optimally positioned in accordance with the physiological and anatomical features of the patient to ensure implant stability, resist dislocation and subluxation of the joint, enhance range of motion and avoid loosening or failure of the components. Accordingly, the liners of prosthetic acetabular components employed in hip surgery have been designed to protrude beyond openings to the cavities of the shells to angularly position the sockets of the liners to provide optimal coverage of the prosthetic femoral heads by the socket components to resist dislocation. Many acetabular components including liners having socket openings therein and shells or cups having cavities therein with openings for receiving the liners with portions of the liners angularly protruding beyond the planes of the cavity openings to angularly position the socket openings to receive a head or ball. The portions of the liners protruding beyond the planes of the cavity openings define angularly protruding lips or overhangs and, in some prosthetic socket components, the liners can be rotated relative to the shells about axes perpendicular to the planes of the cavity openings to change the position of the lips or overhangs to inhibit dislocation.

Currently available acetabular alignment apparatus and procedures generally rely upon either the use of reference locations external to the pelvis of a patient, or direct observation of an implant site by a surgeon during a prosthetic hip joint implant procedure. The reliance upon external references tends to introduce inaccuracies arising from variations in a patient's position on the operating room table. Thus, despite the use of elaborate and expensive equipment in connection with such procedures, reliable and consistent results are not assured. On the other hand, while alignment guides used by surgeons in connection with direct observation techniques are relatively simple and inexpensive, and can expedite the implant procedure, accuracy of alignment depends heavily upon the skill of the surgeon and can vary widely among practitioners in the field.

The instrument of U.S. Pat. No. 6,395,005 provides an alignment apparatus and method which rely upon specific anatomic structures available internally at the pelvis to furnish natural landmarks as references for attaining accurate alignment of an acetabular device at an implant site in the pelvis. However, it is still difficult for the surgeon to position the acetabular to prevent dislocation due to impingement between the femoral component and the acetabular cup.

BRIEF SUMMARY OF THE INVENTION

One aspect of the present invention involves maximizing the range of motion in an artificial hip by ensuring the acetabular cup is installed in its optimal position with respect to the acetabulum, femoral head, and femoral neck. If the cup is installation is not optimal, impingement will occur between the femoral neck and acetabular cup at the limits of articulation. Although implant trialing is a procedure that is performed to check for this fitment issue, it only offers a limited ability to detect this impingement. Since the area cannot be seen, the surgeon has difficulty determining when impingement occurs and must rely solely on feel and experience. The implant trial of the present invention has the ability to detect impingement and indicate its specific location. Once impingement is detected the surgeon can correct any misalignment easily with an impactor. In order to sense when a hip stem impinges on an acetabular cup, three things need to be determined. The first is to determine which components interfere and create the impingement. The second is to locate the regions of contact between the components when installation is not at its optimal position. Lastly, the impingement location needs to be communicated back to the surgeon (outside of the body) via a simple display. This can be accomplished with a plurality of electric sensor contacts located around a periphery of an acetabular cup trial. Separate wires may be connected to each contact.

One aspect of the present invention is the use of a microcontroller with a variety of small resistances and capacitive touch sensors. This allows flexibility during testing as well as much needed room by using less wiring compared to individually wired sensors which of course may be used. It was found that a trial cup with two-piece body design and a "softpot" (soft potentiometer) sensor (resistance touch) can fulfill these requirements. This yields a low cost solution with a practical approach which can be easily manufactured. Since lower cost technologies are used, the acetabular trial can be disposable.

The actuation of the "softpot" sensor mounted within the trial cup, once installed in the body, preferably uses a plurality of flexible actuation "fingers." The "fingers" are created in two sections, one in the trial cup body cavity, and a mating set on the rim of the trial cup The fingers are designed to work together to prevent false signaling ("hits") during normal femoral neck and ball articulation near the impingement edges. A light emitting diode (LED) activation occurs when the neck's stem is articulated and interferes with the top corner of the trial cup.

These aspects of the present invention can be achieved by an acetabular trialing system having a trial acetabular cup having a body with an outer surface, a part-spherical inner surface and a rim extending between the inner and outer surface. The rim includes a plurality of spaced inwardly resiliently deflectable rim members each connected, at a first end, to the outer surface of the body. The part-spherical inner surface has a plurality of spaced resilient deflectable bearing members each having an arcuate inner surface forming part of the body part-spherical inner surface. The bearing members have a first end deflectable towards the body outer surface upon inward deflection. One of the plurality of deflectable rim members is capable of contacting the first end of a corresponding one of the plurality of deflectable bearing members and moving the bearing member towards the body outer surface. An electrical contact device is mounted on the body intermediate the outer surface thereof and the deflectable bearing members so that, upon deflection of the resiliently deflected bearing member towards the body outer surface, a surface of the bearing member contacts the electrical contact device. The electrical contact device is capable of generating a signal when contact is made.

The trial acetabular cup electrical contact element can communicate which particular deflectable bearing member of the plurality of deflectable bearing members has made contact. Preferably the electrical contact element is a soft membrane potentiometer extending around a substantial portion of ortho an entire circumference of an inner surface of the body.

The trial acetabular trialing system further includes a control system for receiving input from the soft membrane potentiometer and determining which deflectable bearing member is making contact therewith.

The trial acetabular trialing system further includes a display device preferably having a circular display capable of receiving input from the control system and displaying which deflectable bearing member is contacting the soft membrane potentiometer.

The circular clock-like display has a plurality of LED lights each corresponding to one of the plurality of deflectable bearing members wherein at least one of the LED lights is activated when contact between the soft membrane potentiometer and the deflectable bearing element is made.

In one embodiment there are 12 deflectable rim elements engageable with twelve deflectable bearing members. The deflectable bearing members form segments of a sphere and form part of the part-spherical inner bearing surface of the body. A surface of each deflectable bearing member facing the body outer surface has a protrusion for contacting the electrical contact device.

Preferably each deflectable bearing member protrusion has a rounded tip for contacting the electrical contact element.

Each deflectable rim member has a free second end which can be deflected into engagement with the free first end of one of the deflectable bearing members. The first end of each rim element is molded to the body outer surface and the first end of the deflectable bearing member is molded, at a polar area, to the body inner part-spherical surface.

This aspect is also achieved by a trial acetabular cup which has a body with an outer surface, a part-spherical inner defining cavity and a rim extending between the inner and outer surface. The rim has a plurality of spaced inwardly resiliently deflectable rim members having a first end connected to the outer surface and a second free end. The part-spherical inner surface has a plurality of spaced resiliently deflectable bearing members. The resiliently deflectable bearing members are spaced by slots extending from a base portion (polar area) of the cavity and having free ends adjacent the second end of the rim members. Each deflectable bearing member has an arcuate inner surface forming part of the body part-spherical inner surface. Upon deflection of one of the plurality of deflectable rim members towards the body cavity the rim member is capable of contacting a corresponding one of the plurality of deflectable bearing members and moving the bearing member towards the body outer surface. An electrical contact device is mounted on the body intermediate the outer surface thereof and the deflectable bearing members so that upon deflection of the resiliently deflected bearing member towards the body outer surface a surface of the bearing member contacts the electrical contact element.

The electrical contact element can communicate to a user which particular rim member makes contact with the corresponding deflectable bearing member of the plurality of deflectable bearing members.

Upon being contacted by a deflectable bearing member the electrical contact element can communicate to a user which particular deflectable bearing member of the plurality of deflectable bearing members has made contact.

A control system is provided for receiving input from the soft membrane potentiometer and determining which deflectable bearing member is making contact therewith.

A display device preferably having a circular display capable of receiving input from the control system and displaying which deflectable bearing member is contacting the soft membrane potentiometer to the surgeon.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

DETAILED DESCRIPTION

Figure 1:
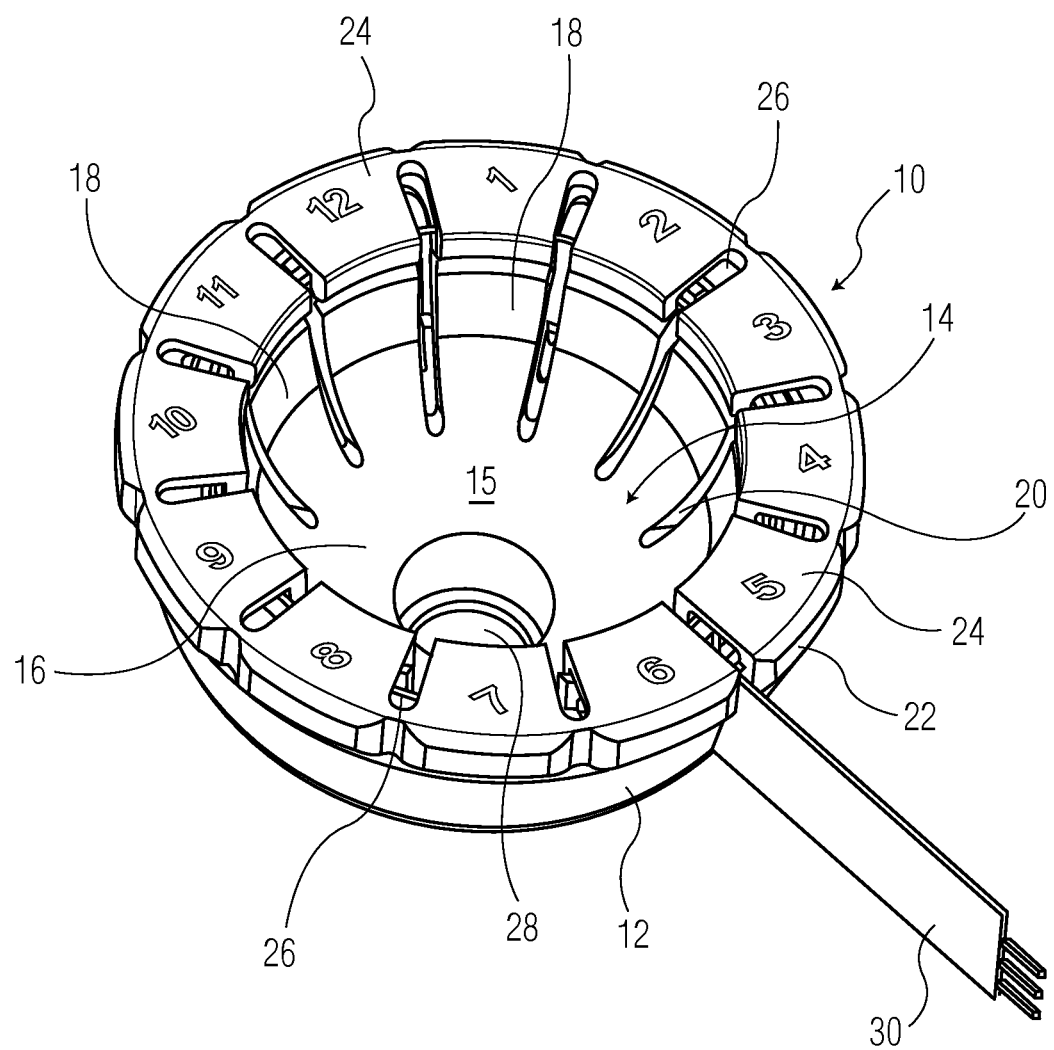
FIG. 1 is an isometric distal view of an acetabular trial cup.

Referring to FIGS. 1-4, there is shown an isometric view of the trial acetabular cup of the present invention generally denoted as 10. Trial cup 10 has an outer shell 12 preferably made of polymeric material and an inner cavity 14, which has a part-spherical wall 15 with a part-spherical inner surface defined by a solid wall portion 16 adjacent the polar region of the cavity which, upon placement in the acetabulum, is the proximal most area of the inner cavity 14. Inner cavity 14 is preferably identical to the ultra-high molecular weight polyethylene bearing inserted in a prosthetic shell which has been implanted in the acetabulum. The inner surface of wall 15 of cavity 14 is further defined by a plurality of deflectable finger-like elements 18, which are separated by slots 20 in wall 15 forming inner cavity 14. As can be seen in FIG. 1, there are preferably 12 finger-like deflectable elements 18 separated by 12 slots 20 all forming wall 15. Also shown in FIG. 1 is a rim 22 of the trial acetabular cup, which extends from an outer surface of shell 12 into the cavity 14. Rim 22 is composed of a plurality of deflectable rim elements 24 separated by slots 26, which slots extend at least part way through rim 22. Again, in a preferred embodiment, there are 12 deflectable rim elements 24, each corresponding to a resiliently deflectable finger-like element 18. The trial cup 10 can either be placed in a trial shell placed in the prepared acetabulum or preferably, in a prosthetic metal acetabular shell already implanted in a prepared acetabulum.

Also shown in FIG. 1 is a through opening 28 at the pole of the inner cavity 14, which allows for reception of a manipulation instrument for positioning trial cup 10 and can be used for fastening the trial to the already implanted acetabular cup shell or trial shell. Also shown in FIG. 1 is electrical lead 30, which connects an electrical sensor element mounted on a surface of the trial cup located between wall 15 and outer surface 12 with a controller as will be described hereinbelow.

Figure 2:
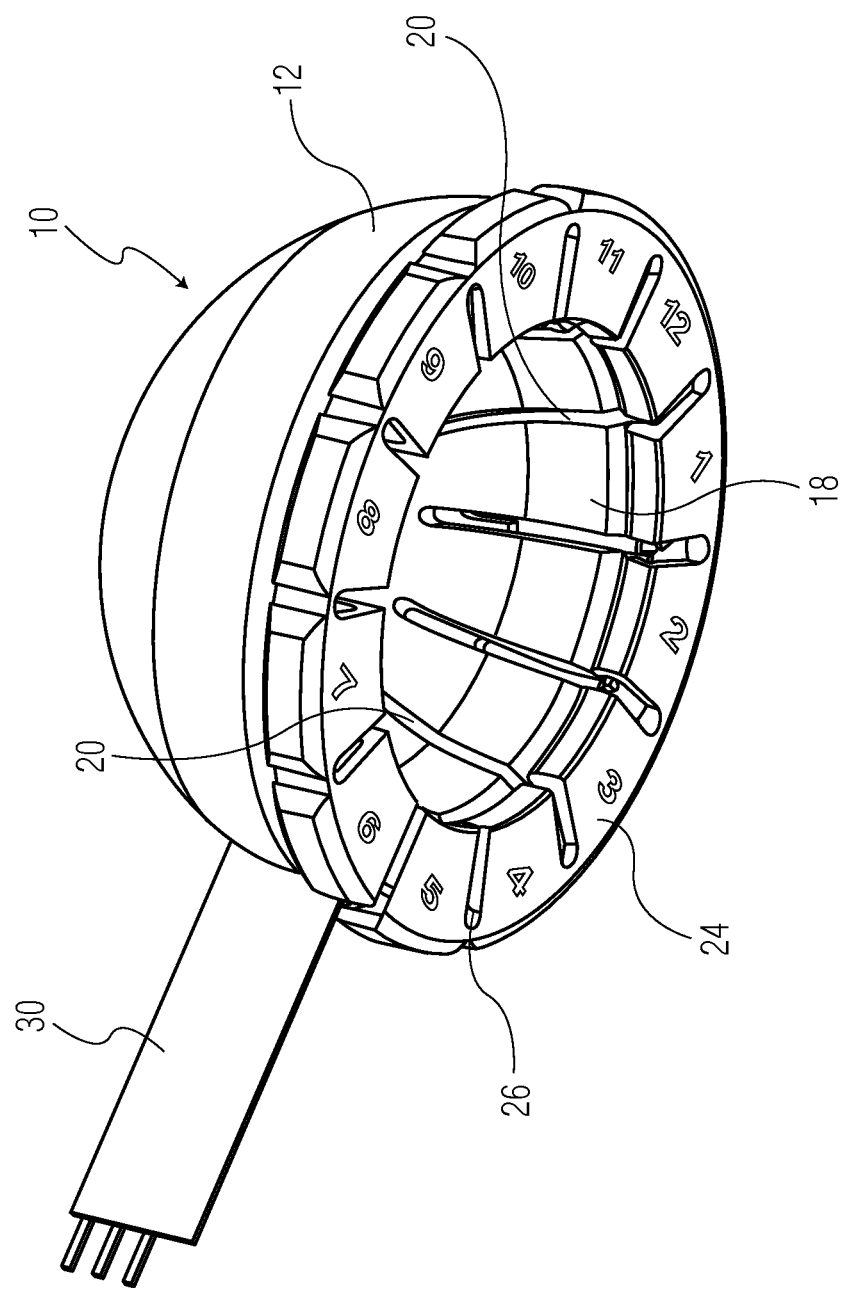
FIG. 2 is the trial acetabular cup of FIG. 1 shown from the side.
Figure 3:
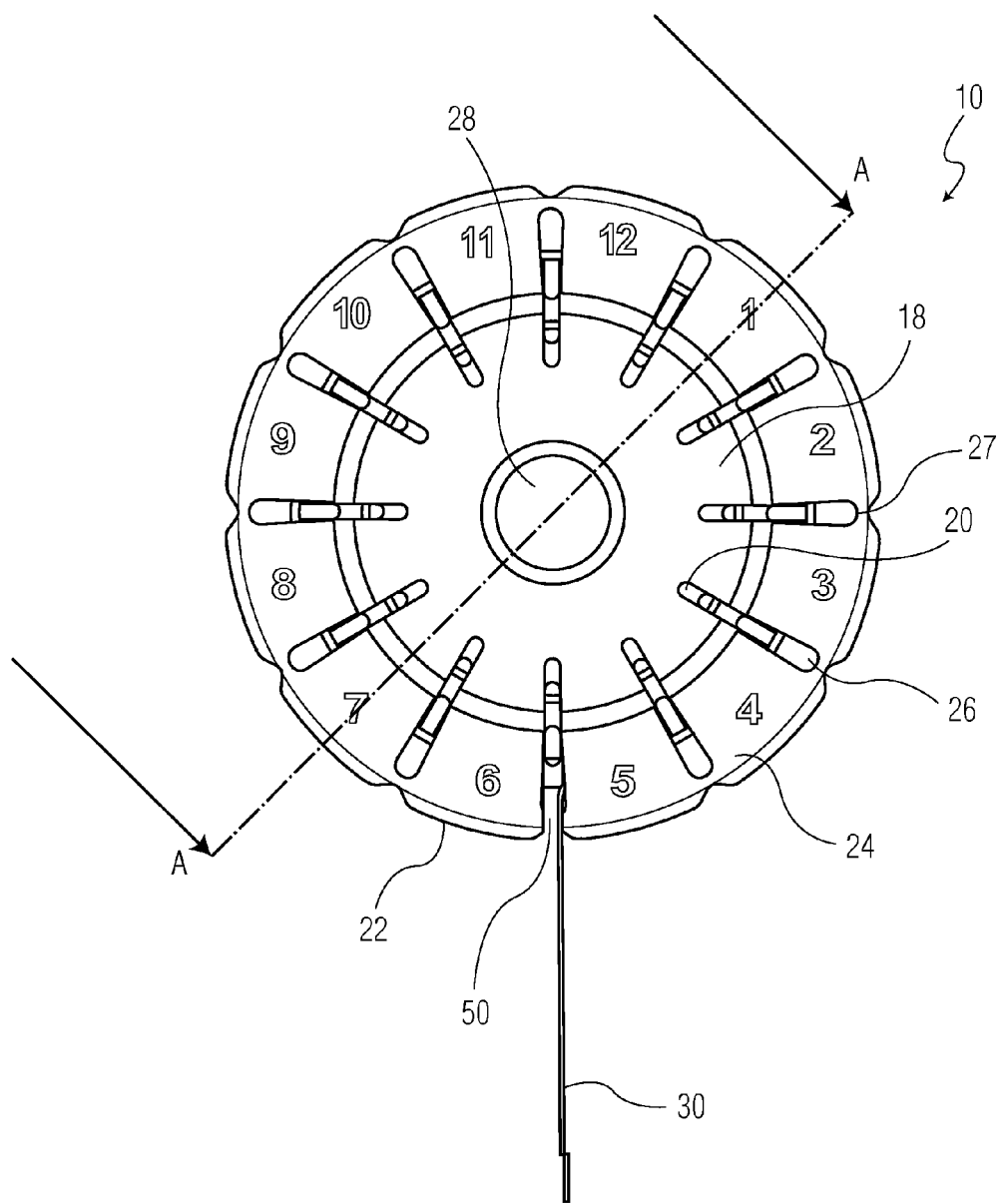
FIG. 3 is a bottom view of the trial acetabular cup of FIGS. 1 and 2.

Referring to FIG. 2, there is shown the trial acetabular cup 10 of FIG. 1 rotated in a direction toward a side view, which shows the outer surface 12 being part-spherical in shape, which would allow its being temporarily mounted in an inner surface of the shell located in the prepared acetabulum. For this purpose, a fastening element is inserted through central opening 28 of FIG. 1 into a threaded bore in the shell. Otherwise the elements shown in FIG. 2 are similar to those shown in FIG. 1. Referring to FIG. 3, there is shown a bottom view of the trial acetabular cup 10 of FIGS. 1 and 2 showing slots 20 and 26 for each of the 12 deflectable rim elements 24 and each of the resiliently deflectable elements 18 aligned so that there are 12 rim elements 24 each corresponding directly to one of the 12 deflectable elements of the wall inner cavity 14. For ease of use, the 12 rim elements 24 are marked with numerals 1 through 12 so, as will be discussed below, the surgeon can identify which rim element 24 of the trial acetabular cup is being contacted by the neck of a trial femoral component during a trial reduction of the joint because an LED display device uses the same numeral for 12 lights. Note that slots 26 may extend only partly through rim 22 leaving a bridge area 27. This is acceptable so long as each rim element 24 can deflect inwardly towards the polar are adjacent aperture 28.

Figure 4:
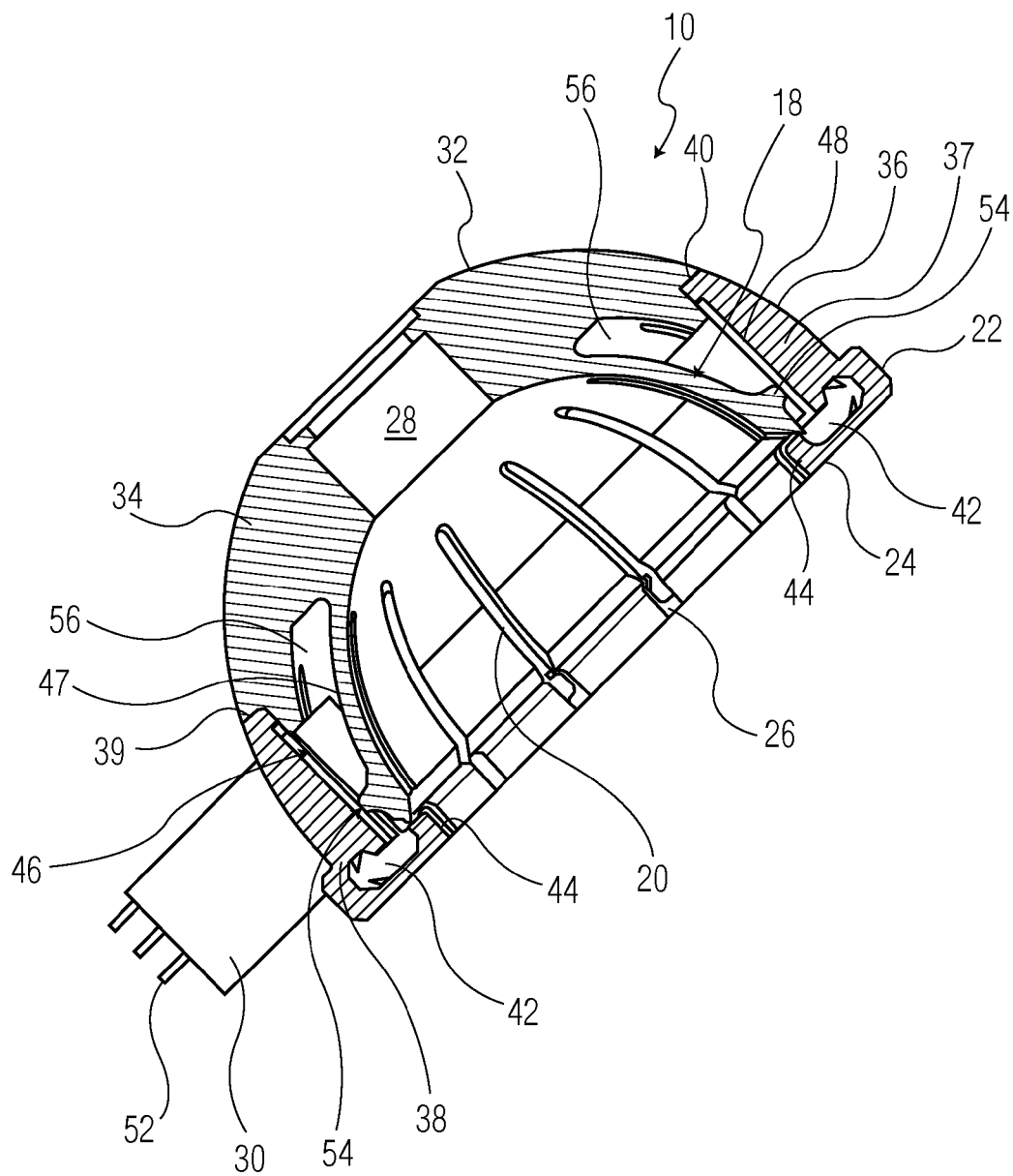
FIG. 4 is a cross-sectional view of the trial acetabular cup of FIG. 3 along lines A-A.

Referring to FIG. 4, there is shown a cross-sectional view of the trial acetabular cup FIGS. 1-3, through lines A-A of FIG. 3. It can be seen that cup 10 includes a body 32, preferably of a polymeric material, which body 32 is comprised of a proximal part 34 and a distal part 36. Part 36 includes rim 22. Proximal part 34 includes deflectable finger-like elements 18 formed monolithically as part of the proximal portion 34. Since the material used to make body 32 is polymeric, elements 34 and 18 are molded, such as by injection molding, as a one-piece (monolithic) construct. Distal portion 36 likewise is molded to include deflectable rim elements 24, which are made one-piece with the remaining circumferential portion 37 of distal body portion 36. Portion 37 has a proximal end 39, which contacts a recessed area 40, which forms a ledge around the circumference of body portion 34. The contacting surface 39 and 40 may be bonded together (after electrical sensor is installed) to thereby form trial acetabular cup 10. Portion 37 is integral or one piece with deflectable rim element 24 and is connected thereto by a deflectable connector portion 38. To allow for the deflecting of rim element 24, a cavity 42 in each distal portion 36 is located between a free end 44 and the connection portion 38 of each deflectable rim portion 24 of distal portion 36 section 37. This allows each deflectable rim element to deflect inwardly towards the pole of inner cavity 14.

Also referring to FIG. 4, there is shown a circumferential soft potentiometer 46, which extends around an inner surface 48 of section 37 of body portion 36. This soft potentiometer known as SoftPot may be obtained from Spectra Symbol, 3101 W. 2100 S., Salt Lake City, Utah 84119. Potentiometer 46 extends almost entirely around circumferential inner surface 48 and is connected to lead 30, which exits through a slot 50 in body 32. Typically, lead 30 includes three thin copper wires 52, which connect to a controller.

Deflectable arms 18 include a protruding polymer portion 54, which can contact soft potentiometer 46 when deflectable element 18 is moved toward the outer surface of distal body portion 36 by member 24. As will be discussed below, this occurs when deflectable rim portion 24 is deflected inwardly toward the base or pole area of cavity 14 upon impingement of the neck of a femoral component during the trial reduction. In order to facilitate the deflection of deflectable element 18, a cavity 56 extends circumferentially of an outer surface 47 of deflectable element 18 within proximal body portion 34. As indicated above, both body portions 34 and 36 can be separately injection molded and then joined after the mounting of the soft potentiometer 46 in a recessed area or a groove formed on an inner surface of outer shell 12. Soft potentiometers are well known and produce a varying resistance depending on which deflectable element 18 is contacting the potentiometer 46 via protrusion 54. Obviously, it is also possible to have individual contact elements associated with each deflectable element 18, however, this would require separate wiring to each of the 12 separate electrical contact elements.

Figure 5:
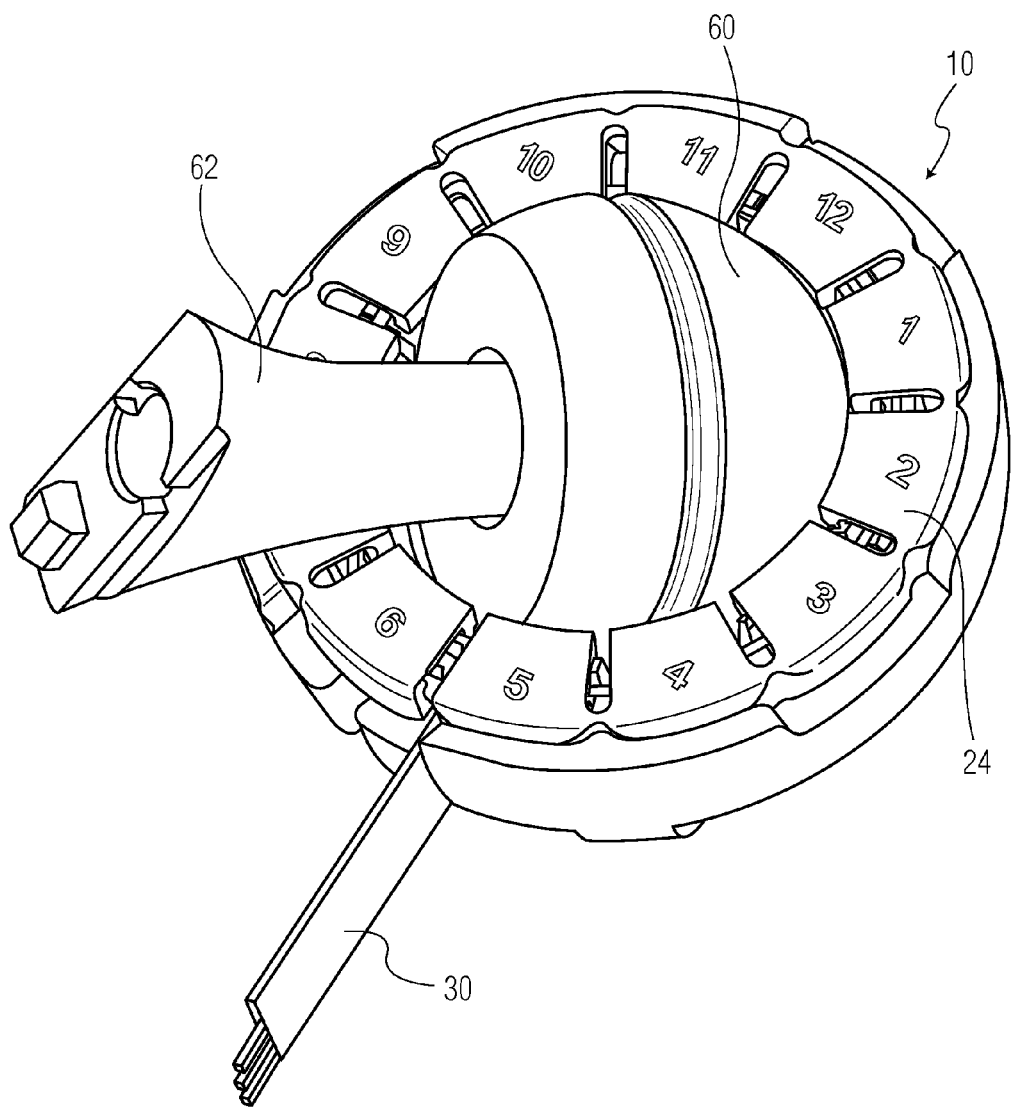
FIG. 5 is an isometric view showing the acetabular trial cup of FIGS. 1-4 including the proximal portion of a prosthetic femoral component, including a femoral head, mounted within the cup.
Figure 6:
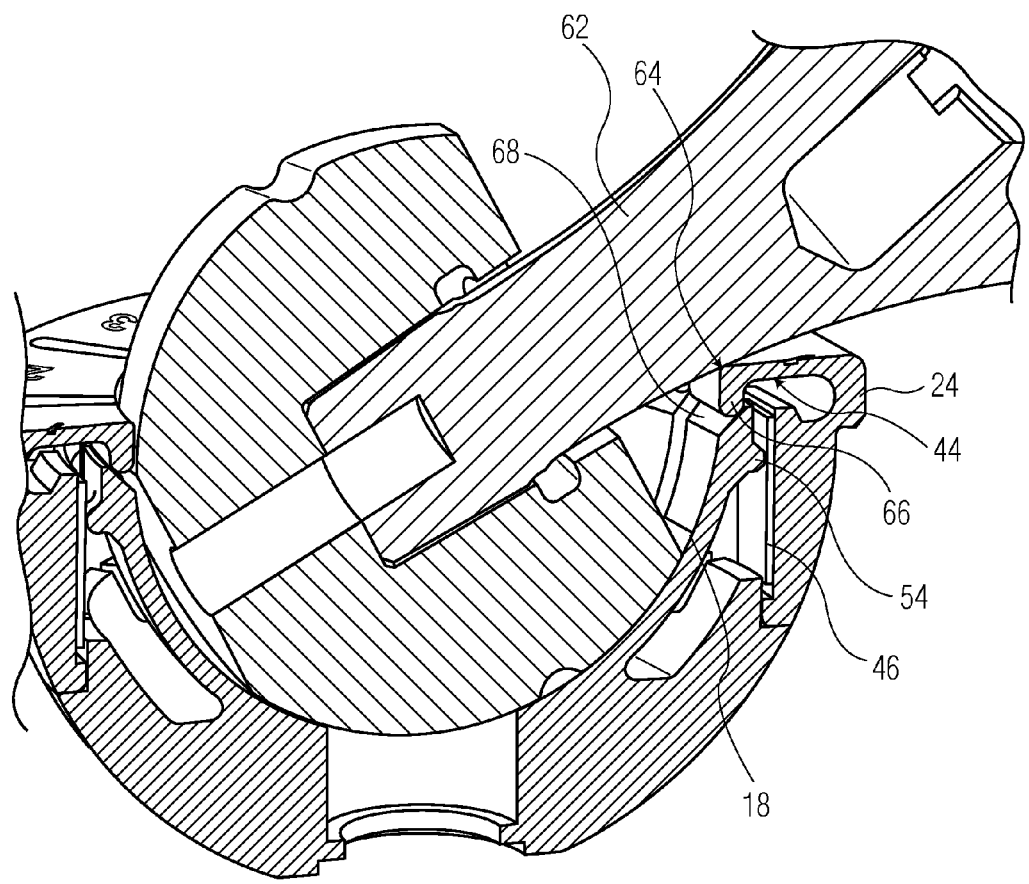
FIG. 6 is a cross-sectional view of the assembly of FIG. 5 showing the neck of the hip stem impinging on one of the rim elements of the trial acetabular cup.

Referring to FIG. 5, there is shown a neck and head portion of a typical trial or actual femoral component mounted in trial acetabular cup 10. A trial head 60 connected to a femoral component neck portion 62 is mounted within cavity 14 of cup 10 and can be rotated in any direction because of the part-spherical nature of both the head 60 and cavity 14. When neck 62 contacts a rim element 24 such is deflected inwardly toward the pole of cavity 14. The free end 44 of element 24 then contacts flexible element 18 thereby moving it and its protrusion 54 into contact with potentiometer 46. This can be best seen in FIG. 6, which shows one area 63 of neck 62 contacting a corner 64 of rim element 24 thereby deflecting free end 44 such that a tip 66 thereof contacts an angled surface 68 on the free end of deflectable element 18, which then moves protrusion 54 into contact with soft potentiometer 46.

Figure 7:
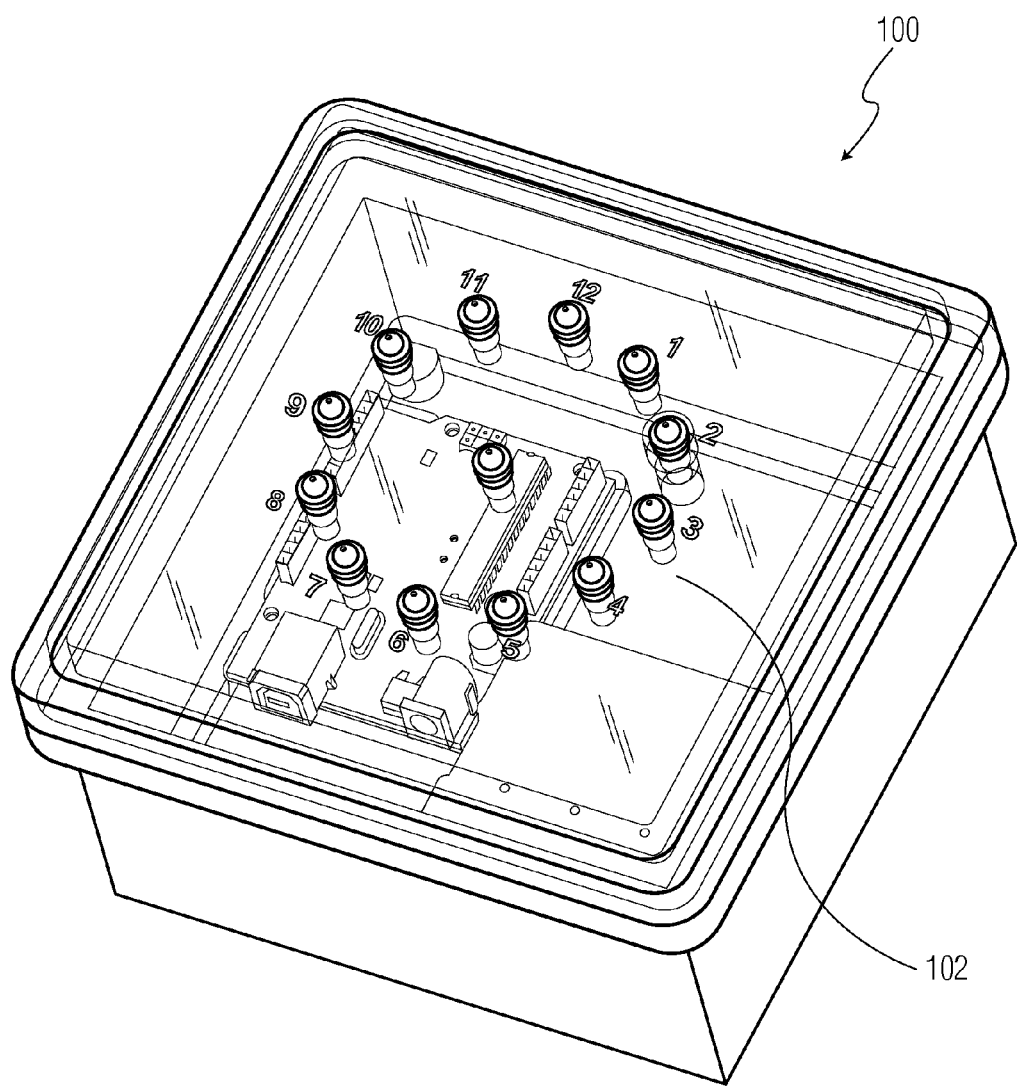
FIG. 7 shows a control system for displaying which of the rim elements is being contacted by the femoral neck of FIG. 6 via a light emitting diode (LED) display.
Figure 8:
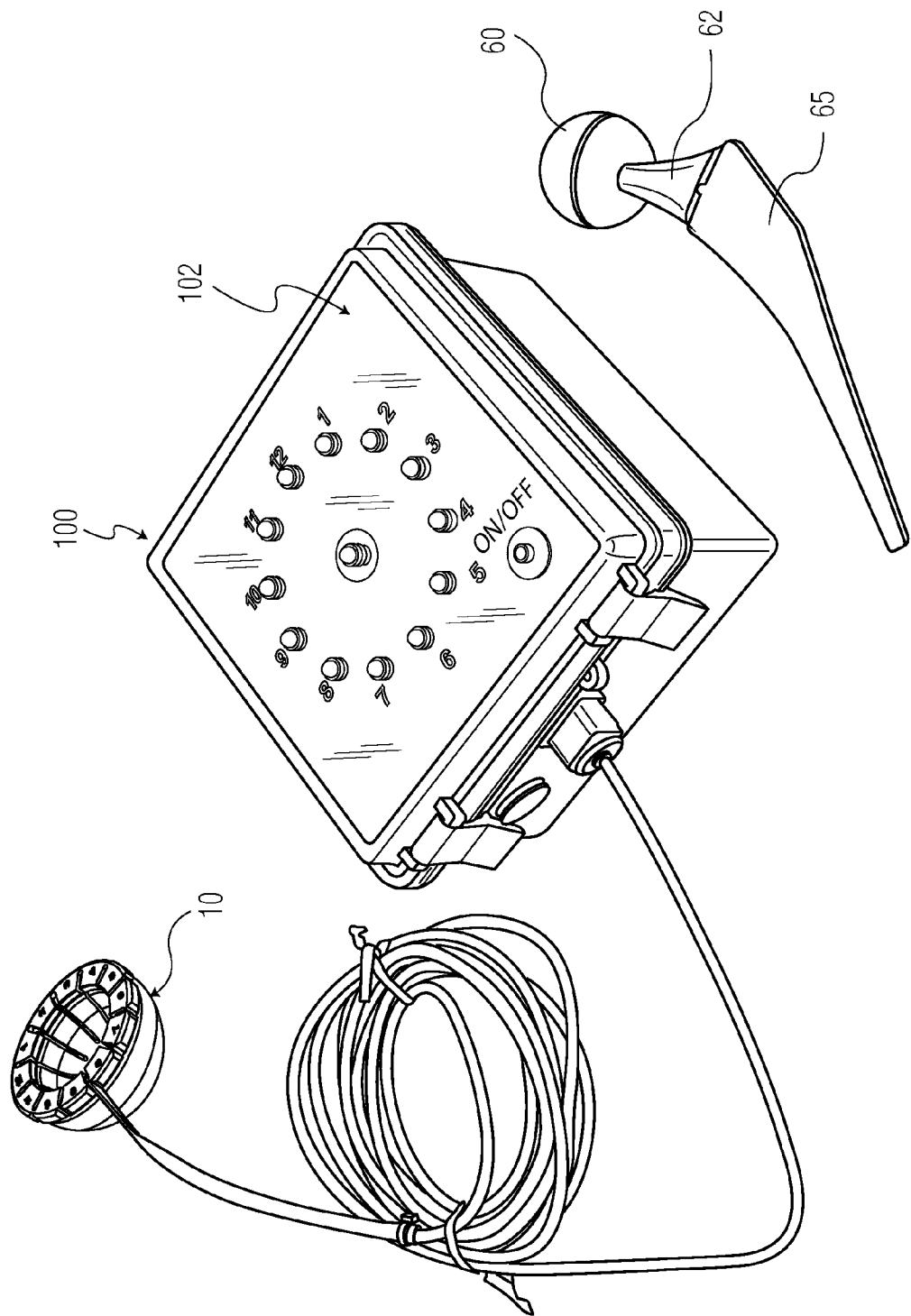
FIG. 8 shows a kit of components comprising the acetabular trialing system including the trial acetabular cup of FIGS. 1-4, a trial femoral component shown in part in FIGS. 5 and 6 and the controller of FIG. 7.

As can be seen in FIGS. 7 and 8, there is a controller generally designated as 100, which provides a small current to the potentiometer and can detect changes in current flow due to changes in resistance depending on which deflectable element 18 makes contact with potentiometer 46. Controller 100 includes 12 light-emitting diodes (LED) 102, which correspond to the preferably 12 deflectable elements 18 and 12 rim elements 24. Obviously fewer or more deflectable elements can be used. These LEDs are numbered in a corresponding manner to the numbers on rim elements 24 so that the surgeon knows which deflectable rim element 24 is in being contacted by the neck 62 depending on which light is illuminated. If two elements light up simultaneously, the surgeon knows that the neck is impinging at a point intermediate the two numbered deflectable rim elements. Referring to FIG. 8, there is shown the entire acetabular trialing system, including cup 10, control box 100, and femoral trial component with neck 62 and head 60, including a stem 65. As shown in FIG. 8, stem 65 may be part of a broach or rasp used to prepare the femoral canal.

The wire between the trial cup and the LED display clock would extend out of the wound. The LED clock would be visible as a trial reduction is performed. A trial range of motion (ROM) is performed, LED lights light, then surgeon determines if he want to adjust cup in a way that would be such that would avoid the LED light from lighting. The operation would be re-performed until the surgeon is satisfied with the patient ROM and either the lack of impingement (LED light lighting up), or that the leg ROM is acceptable even though there is identified impingement.

Another important aspect of this invention is that the impingement is identified after the femoral stem is placed in the femur. It takes into account the actual position of the femoral stem (trial stem or actual implant) which is important as the stem neck does not always recreate the natural body bony femoral neck anatomy. Also, that currently when doing a trial ROM, the surgeon may detect that there is ROM resistance due to impingement, but he currently does not know if it is due to the neck of the stem impinging on the edge of the trial (or actual implant) or is it due to bony impingement, or soft tissue impingement/resistance. This invention addresses this since if the trail cup is contacted an LED lights.

Figure 9:
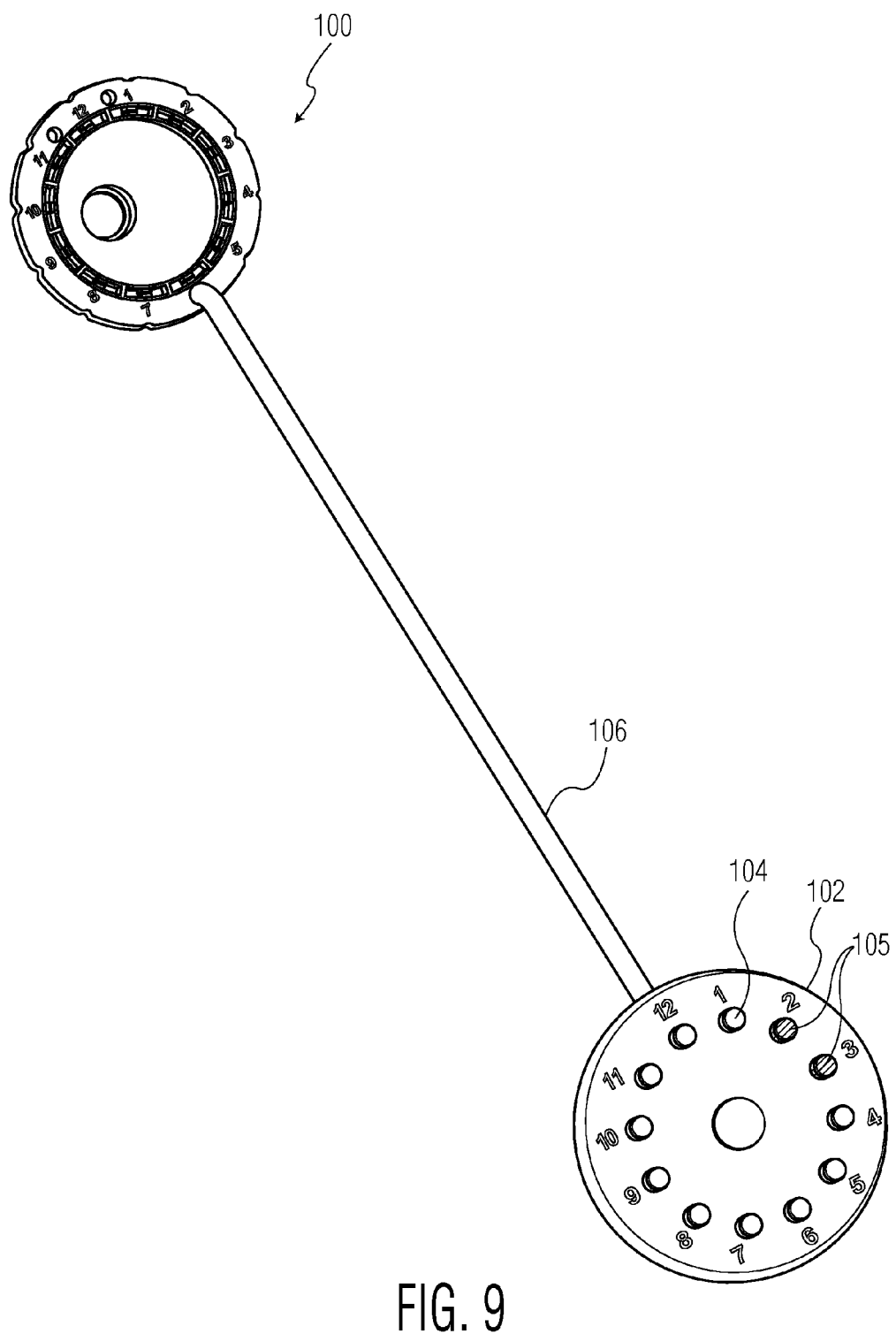
FIG. 9 shows an alternate embodiment of the present invention showing the trial acetabular cup electrically connected to a clock-like display device.

Referring to FIG. 9, there is shown a trial acetabular cup 100 connected to a clock-like device 102 which includes 12 LED lights 104. The lights 104 are connected to trial acetabular cup 100 by a cable 106. As shown in FIG. 9, the display device 102 includes 12 LEDs 104.

Figure 10:
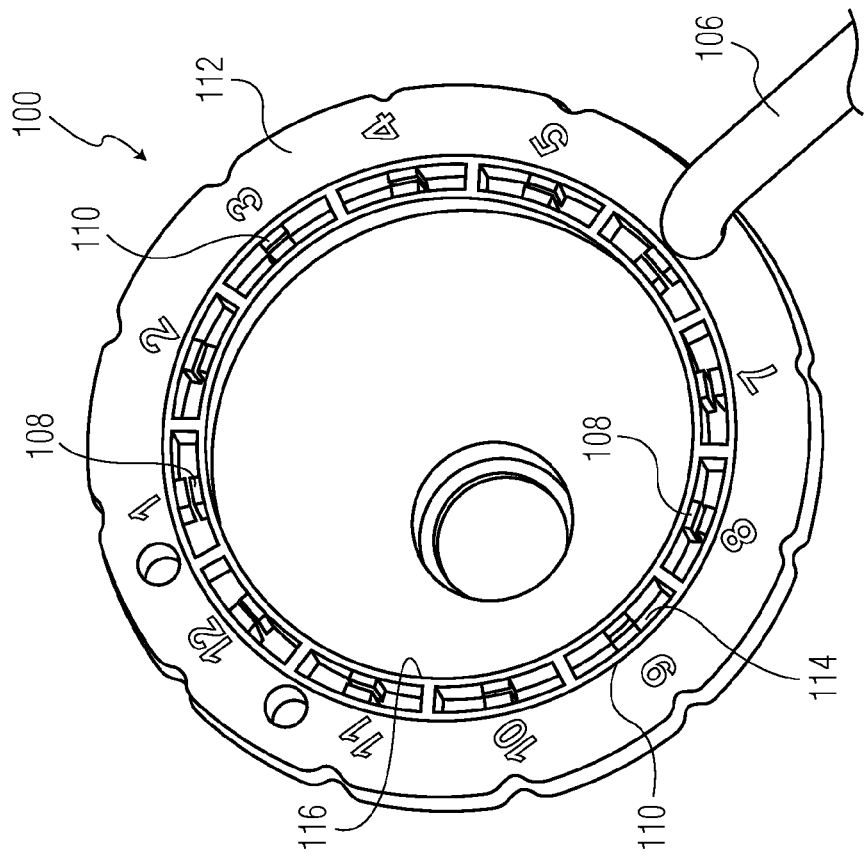
FIG. 10 is an enlarged view of the trial acetabular cup shown in FIG. 9.

Referring to FIG. 10, there is shown an enlarged view of acetabular trial cup 100 which includes 12 resiliently deflectable contact elements 108 which contact electrical sensors 110 mounted on a rim 112 of cup 100. As can be seen in FIG. 10, there are 12 positions spaced at 30° intervals around the 360° circumference around inner surface 114 of rim 112.

Each electrical contact sensor 112 is connected via a dedicated wire which feeds cable 106. The 12 wires carry electrical signals to the LEDs 104 on display 102. Electrical contact elements 108 may be mounted on a resiliently deflectable polymeric ring 116 which can deflect outwardly towards surface 114 of rim 112 when contacted by a femoral component neck. Upon this outward deflection, contact element 108 contacts sensor 110 to produce the signal. Since there are 12 individual wires each connected to a sensor 110, the signal generated will indicate which area of the rim circumference is making contact with the neck. Of course, if no impingement occurs between the trial cup and the femoral component stem, no light will be lit.

Figure 11:
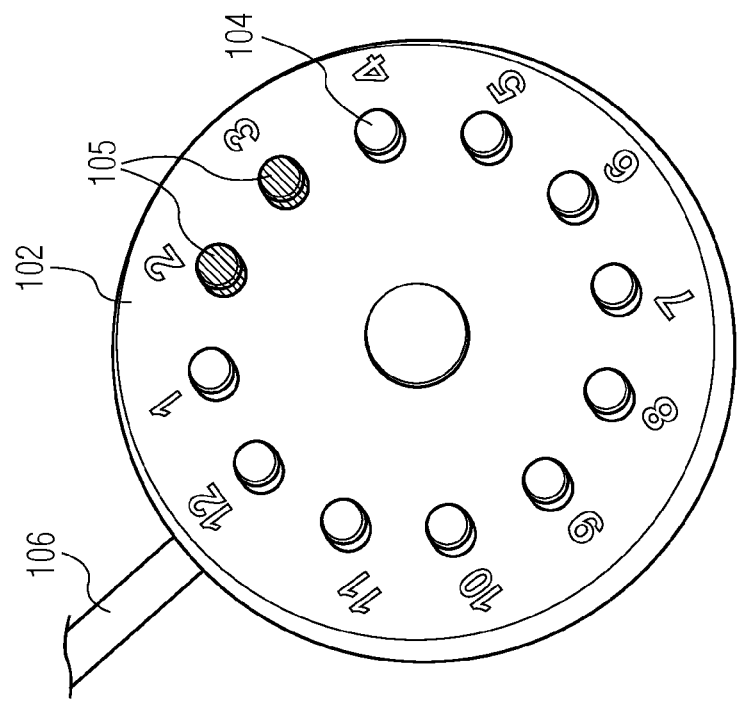
FIG. 11 is an enlarged view of the clock-like LED display device of FIG. 9 with positions 2 and 3 lit.

Referring to FIG. 11 there is an enlarged view of the clock-like display 102 shown in FIG. 9. As can be seen, there are 12 LEDs 104 corresponding to the 12 positions on cup 110. These LEDs are connected by wires to the electrical contact sensors 110 by cable 106. Cable 106 also carries an input current which powers the lights when contact between elements 108 and sensor 110 occur. As can be seen in FIG. 11, LEDs 2 and 3, labeled 105, are lit which would occur when the neck of the femoral component impinges the area of rim 116 between numerals 2 and 3 of trial cup 100.

In the use of either embodiment 10 or 100 of acetabular cup trial, the acetabulum is first prepared by reaming and the femur is prepared by, for example, broaching. A trial shell or actual prosthetic shell implant is press-fit into the reamed acetabular socket. The disposable insert trial cup 10, 100 is then placed therein with the electrical cable extending outside of the wound. A femoral component is then placed in the broached femur with a head and neck trial placed thereon and the joint is reduced by the surgeon. The surgeon then conducts a trial range of motion test to see which lights, if any, light on the display device to indicate impingement with the LEDs being lit designating where the impingement occurs. If unacceptable impingement occurs, the femoral component and head is distracted from the trial cup 10, 100 and the acetabular shell is repositioned in the acetabulum as needed. The range of motion test is repeated until the surgeon is satisfied with the shell position. The surgeon then marks the bone location for the shell so that, if a trial shell was used, the prosthetic shell can be located in the correct position. Of course if the actual prosthetic acetabular shell was used during the test, then this step can be eliminated.

It is also possible to use, instead of or in addition to lights, the electrical contact to trigger a sound, like a ring or buzz as an audible induction of impingement. It is also possible to have a controller which once the lights are lit they stay on after the electrical connection is broken. This would allow the user to see which region had contact without having to recall which lights had been on. A reset button would turn off the lights.

Rather than have the indicator of impingement of the implant or trial neck on the trial shell be a light or sound triggered by electrical contact, the indicator could simply be a deformation of a malleable portion of the trial insert for example around the rim. For example, clay would have sufficient mechanical integrity to be placed into the operative site but would also be deformed if it came into contact with a neck during a range of motion determination. A metal or polymer material would also be suitable if it had similar mechanical properties. Any deformation to the malleable rim that occurs during reduction of the trial (i.e. placing the femoral head (trial or implant) into the trial insert should be avoided, but if it does occur it will be different in appearance to the type of deformation caused by impingement of the femoral component neck (trial or implant) on the malleable rim.

Figure 12:
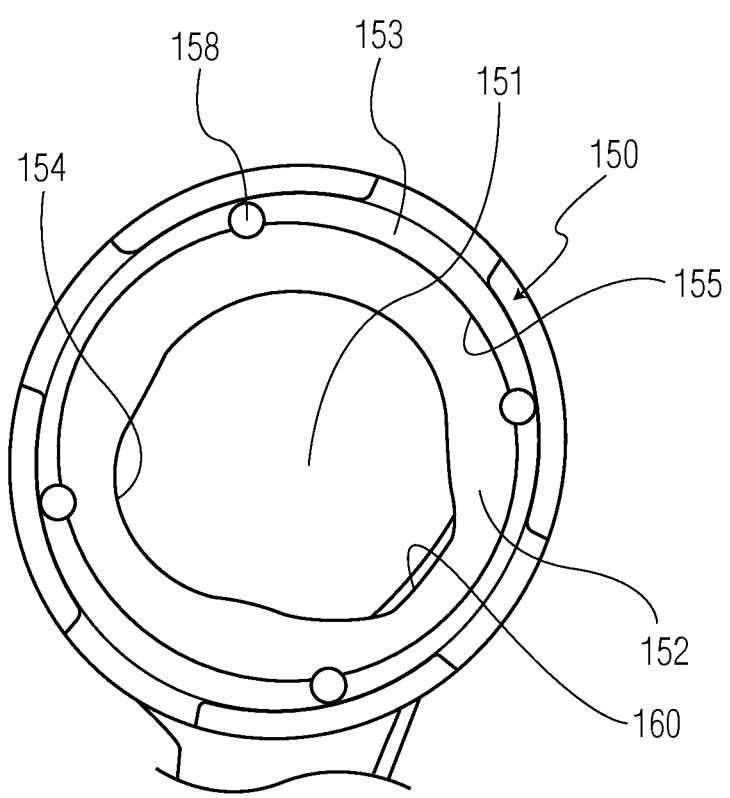
FIG. 12 is a bottom view of an acetabular cup trial including an outer shell and an inner malleable insert capable of indicating the location of an impingement with the neck of a prosthetic or trial femoral component.

After placement of the malleable trial insert into either an implant or trial shell and subsequent range of motion testing of the trial joint, any place where the neck impinged on the malleable trial insert rim would be readily apparent. The shell could then be repositioned based on that information. This step could be performed multiple times in iterative fashion if deemed necessary by the surgeon with each subsequent adjustment moving the shell closer to the optimal position. If multiple iterations are necessary, the same malleable trial insert may be able to be used each time, but the surgeon may also choose to use a new malleable trial insert for each iteration since the new trial insert will not have any deformed spots on the rim from previous iterations. Such an implant is shown in FIG. 12 in which there is shown a trial acetabular cup generally denoted as 150 having a cavity 151. The cup includes a metal shell 153 having an inner rim area 155 with a malleable insert 154 located around the circumference of the inner cavity 151 at least in the area of the rim 155. When the trial or actual femoral component neck impinges on the malleable element 154 a depression 160 is formed thereon. Anti-rotation elements 158 are provided to ensure that the malleable insert 154 does not rotate with respect to shell 153 when the femoral component neck makes contact therewith.

Another possibility is rather than having the rim of the trial insert deform when the neck makes contact, the entire insert could rotate in the shell. Friction between the insert and shell would serve to hold the insert in its new position once the rotation had occurred. The friction could be provided and controlled by a center post component that is threaded into the shell and captures the trial insert in the shell without fixing the trial insert in one angular orientation. The threaded apical holes on many commercially available acetabular implants and trials such as Trident® cup system by Stryker Corp. used to aid insertion of the components could easily accommodate the center post component.

Figure 13:
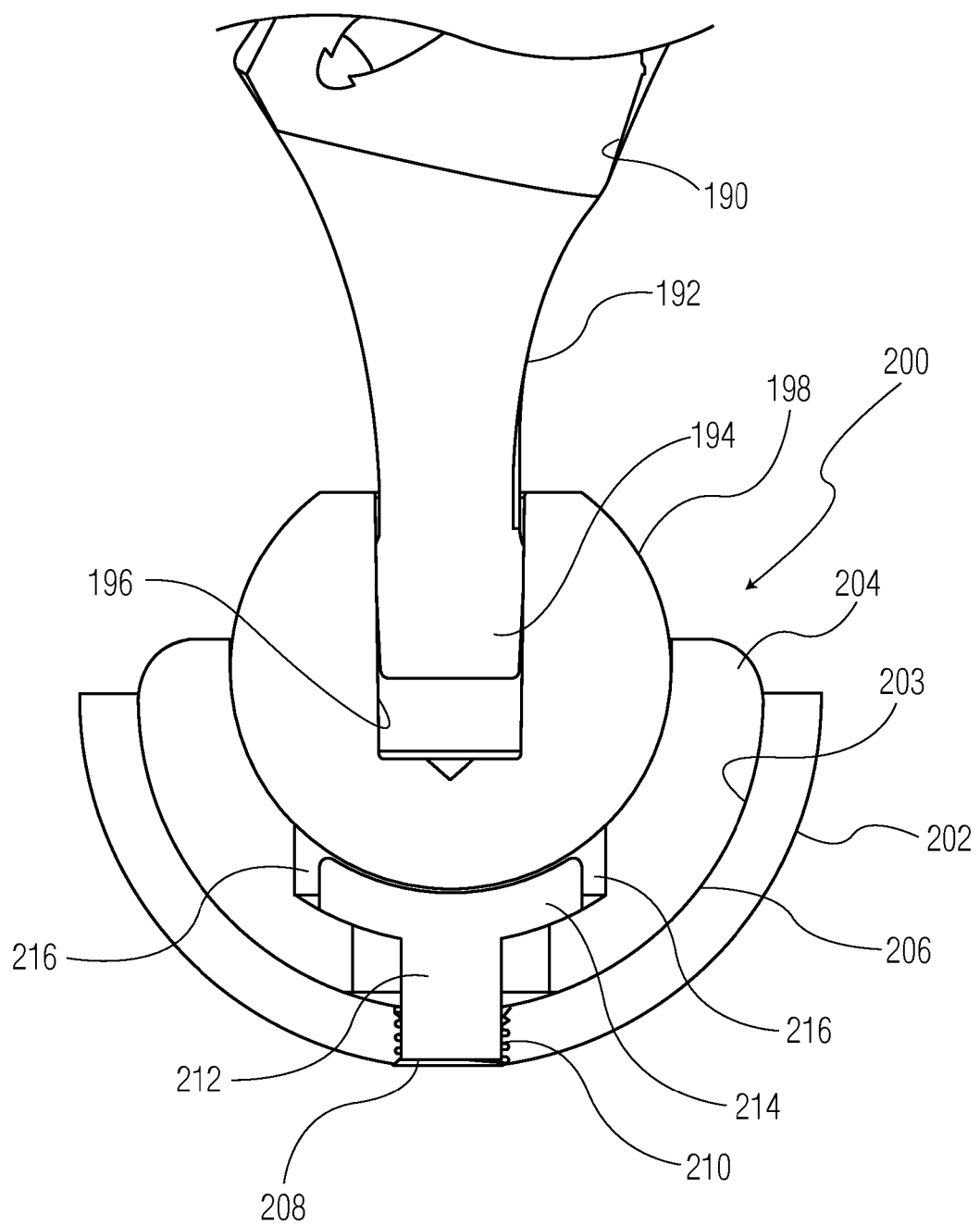
FIG. 13 is cross-sectional view of an alternate embodiment of a trial acetabular cup in which an insert may be repositioned within the acetabular cup shell by impingement with the neck of a trial or actual femoral component which insert then remains in a fixed position when the impingement is removed.
Figure 14:
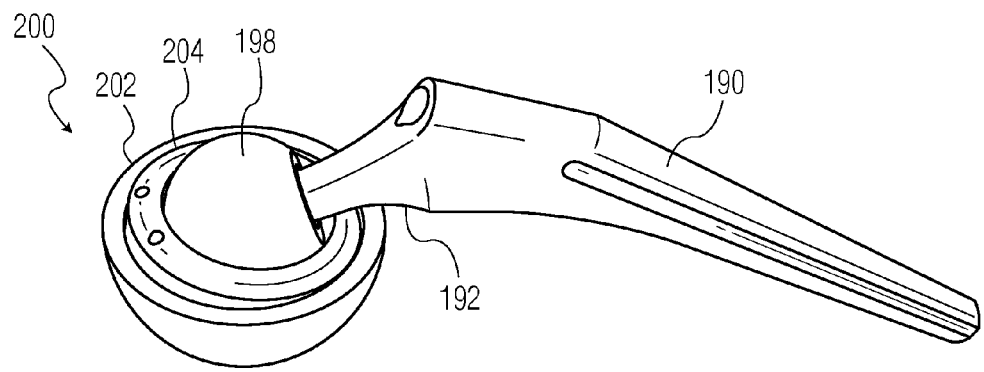
FIG. 14 is an isometric view showing the neck of the trial or actual femoral component contacting the insert shown in FIG. 13.
Figure 15:
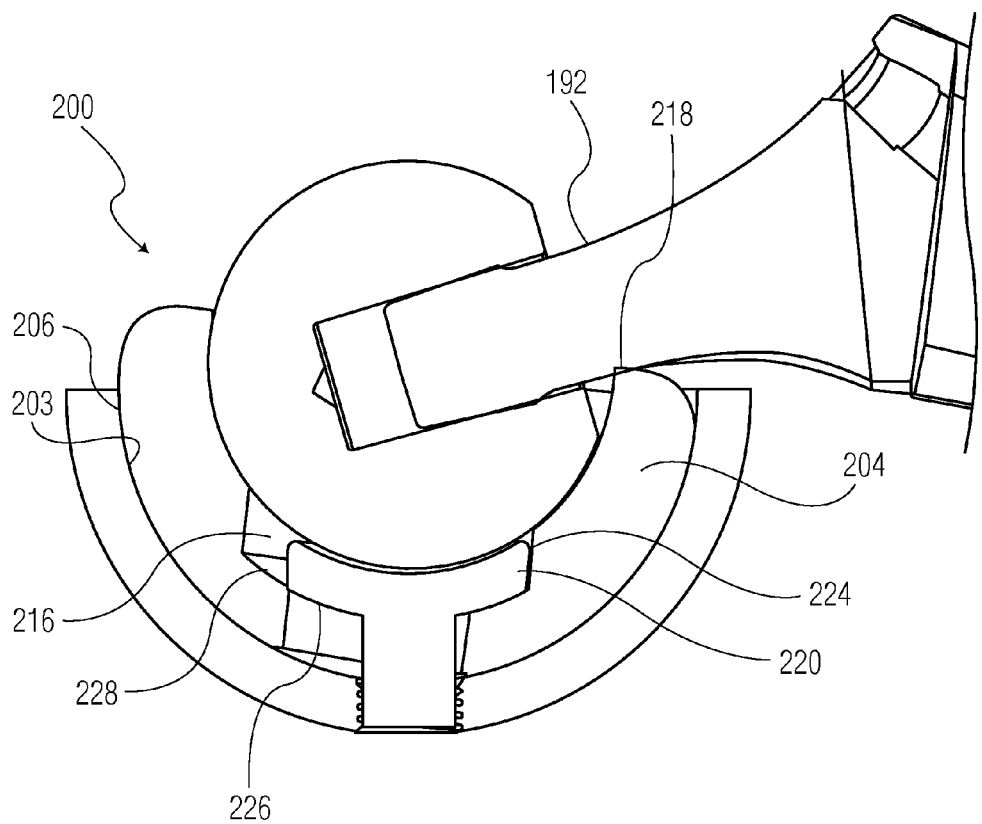
FIG. 15 is a cross-sectional view similar to that of FIG. 13 in which the neck of the prosthetic femoral component or trial femoral component is impinging against the insert shown in FIGS. 13 and 14.

The rotatable trial insert would preferably be initially aligned with the shell into which it is placed in that the face (equator) of the trial insert would be parallel to the face (equator) of the shell and held there by friction. After trial reduction of the joint followed by range of motion testing, the face of the rotatable insert may be moved into a position that is no longer parallel to the face of the shell. The position of the face of the insert could then serve as a guide to the proper orientation of the face of the shell that will maximize range of motion of the joint and minimize the potential for impingement of the femoral neck implant and acetabular shell implant. Such a rotatable insert is shown in FIGS. 13-15 and is generally denoted as 200. Referring to FIG. 13 there is shown the trial or actual femoral component 190 including a neck section 192 and a conically tapered trunnion 194. The conically tapered trunnion 194 mates with a conically tapered female bore 196 of a prosthetic femoral head 198.

The trial acetabular cup 200 includes an outer shell 202 with a part-spherical inner surface 203 in which an insert 204 is mounted. Insert 204 has a part-spherical outer surface 206 which can rotate on surface 203. Cup 202 includes a polar region with a bore 208 which includes threads 210. Threaded bore 208 in turn receives a center post 212 which has a flange portion 214 capable of sliding in all directions within a groove 216 formed within the polar area of insert 204. Post 212 produces sufficient force between surfaces 203 and 206 to develop a frictional force which maintains cup 204 in a position within shell 202 even after relative rotation therebetween.

Referring to FIGS. 14 and 15 this situation is shown when the neck 192 of femoral component 190 contacts surface 218 as shown in FIG. 15. This contact causes insert 204 to be rotated for example to a position wherein an end 220 of post 212 contacts surface 224 of recessed area 216 within insert 204. Because of the friction produced between surfaces 203 and 206, by a surface 226 of post 212 contacting surface 228 of shell recess 216, the insert 204 remains in the position produced by the impingement of neck 192 against surface 218 even after the femoral component 190 is moved to a position in which the neck 192 is no longer impinging against insert 204.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An acetabular cup trialing system comprising:
    a body having a spherical inner cavity surrounded by a circumferential rim;
    an electrically conductive contact sensor connected to a power source located on the circumferential rim, the contact sensor extending around a circumference of the rim and capable of producing an electrical signal when contacted, the electrical signal varying depending on the location along the contact sensor; and
    a plurality of resiliently deflectable contact elements spaced around the circumference of the rim and spaced radially inwardly of the contact sensor towards the inner cavity, an outward deflection of the deflectable contact element is configured to move the element into contact with the contact sensor to produce the electrical signal; and
    a display device connected to the contact sensors for indicating which of the deflectable contact elements has been deflected.

2. The acetabular trialing system as set forth in claim 1 wherein there are twelve resiliently deflectable contact elements spaced at 30 degree intervals around the circumference of the rim.

3. The acetabular trialing system as set forth in claim 2 further comprising a control system associated with the display device for receiving input from the contact sensor and determining which deflectable bearing member is making contact therewith.

4. The acetabular trialing system as set forth in claim 3 wherein the contact sensor is a soft membrane potentiometer and the display device has a circular display capable of receiving input from the control system and displaying which deflectable bearing member is contacting the soft membrane potentiometer.

5. An acetabular cup trialing system comprising:
    a trial acetabular cup having a body comprising an outer surface, a part-spherical inner surface and a rim extending between the inner and outer surface, the rim comprising a plurality of spaced resiliently deflectable rim members each connected at a first end to the body outer surface, the part-spherical inner surface comprising a plurality of spaced resiliently deflectable bearing members each having an arcuate inner surface forming part of the body part-spherical inner surface, the deflectable bearing members having a first end deflectable towards the body outer surface; upon deflection, one of the plurality of deflectable rim members is capable of contacting the first end of a corresponding one of the plurality of deflectable bearing members and moving the bearing member towards the body outer surface; and an electrical contact sensing device connected to a power source mounted on the body intermediate the outer surface thereof and the deflectable bearing member, the deflectable bearing members are configured to contact the electric contact sensing device upon deflection towards the body outer surface, the contact sensing device having a variable output depending on which of the bearing members contact the electrical contact sensing device.

6. The acetabular trialing system as set forth in claim 5 wherein the electrical contact device communicates which particular deflectable bearing member of the plurality of deflectable bearing members has made contact.

7. The acetabular trialing system as set forth in claim 6 wherein the electrical contact element is a soft membrane potentiometer extending around an entire circumference of an inner surface of the body.

8. The acetabular trialing system as set forth in claim 7 further comprising a control system for receiving input from the soft membrane potentiometer and determining which deflectable bearing member is making contact therewith.

9. The acetabular trialing system as set forth in claim 8 further comprising a display device having a circular display capable of receiving input from the control system and displaying which deflectable bearing member is contacting the soft membrane potentiometer.

10. The acetabular trialing system as set forth in claim 9 wherein the circular display comprises a plurality of light emitting diode (LED) lights each corresponding to one of the plurality of deflectable bearing members wherein at least one of the LED lights is activated when contact between the soft membrane potentiometer and the deflectable bearing element is made.

11. The acetabular trialing system as set forth in claim 5 wherein the electrical contact element is a continuous soft membrane potentiometer extending around an inner circumference of the trial acetabular cup body.

12. The acetabular trialing system as set forth in claim 5 wherein there are 12 deflectable rim elements engageable with twelve deflectable bearing members.

13. The acetabular trialing system as set forth in claim 12 wherein these 12 deflectable rim and bearing members.

14. The acetabular trialing system as set forth in claim 5 wherein the deflectable bearing members form segments of a sphere and form part of the part-spherical bearing surface of the body.

15. The acetabular trialing system as set forth in claim 5 wherein a surface of each deflectable bearing member facing the outer surface has a protrusion for contacting the electrical contact member.

16. The acetabular trialing system of claim 15 wherein each deflectable bearing member protrusion has a rounded tip for contacting the electrical contact element.

17. The acetabular trialing system as set forth in claim 5 wherein each deflectable rim member has a second free end which can be deflected into engagement with the first end of one of the deflectable bearing members.

18. A acetabular trialing system comprising:
a hip femoral component;
a trial acetabular cup having a body comprising an outer surface, a part-spherical inner defining cavity and a rim extending between the inner and outer surface, the rim comprising a plurality of spaced resiliently deflectable rim members having a first end connected to the body and a second free end, the part-spherical inner surface comprising a plurality of spaced resiliently deflectable bearing members, the resiliently deflectable bearing members spaced by slots extending from a base portion of the cavity and having free ends adjacent the second end of the rim members, each bearing member having an arcuate inner surface forming part of the body part-spherical inner surface, the plurality of deflectable rim members are deflectable towards the body inner cavity by contact with the femoral component, upon deflection rim members are capable of contacting one of the plurality of deflectable bearing members and moving the bearing member towards the body outer surface; and
an electrical contact sensing element connected to a power source mounted on the body intermediate the outer surface thereof and the deflectable bearing member, deflection of the resiliently deflected bearing member towards the body outer surface by the femoral component contact with the deflectable rim-member is configured to cause a surface of the bearing member to contacts the electrical contact sensing element.

19. The acetabular trialing system as set forth in claim 18 wherein the electrical contact element communicates to a user which particular deflectable bearing member of the plurality of deflectable bearing members has made contact.

20. The acetabular trialing system as set forth in claim 19 further comprising a control system for receiving input from the soft membrane potentiometer and determining which deflectable bearing member is making contact therewith.

21. The acetabular trialing system as set forth in claim 20 further comprising a display device having a circular display capable of receiving input from the control system and displaying which deflectable bearing member is contacting the soft membrane potentiometer.

22. The acetabular trialing system as set forth in claim 19 wherein the electrical contact element is a continuous soft membrane potentiometer extending around an inner circumference of the trial acetabular cup body.

23. The acetabular trialing system as set forth in claim 18 wherein there are 15 deflectable rim elements engageable with twelve deflectable bearing members.

24. The acetabular trialing system as set forth in claim 18 wherein the deflectable bearing members form segments of a sphere and form part of the part-spherical bearing surface of the body.

* * * * *